(12) United States Patent
Miller et al.

(10) Patent No.: US 6,355,630 B1
(45) Date of Patent: Mar. 12, 2002

(54) ESTRA-1,3,5(10)-TRIENE-7α-THIOETHERS

(75) Inventors: Chris P. Miller, Wayne, PA (US); Ivo Jirkovsky, Nanuet, NY (US); Bach Dinh Tran, Mt. Airy, MD (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/170,355

(22) Filed: Oct. 13, 1998

Related U.S. Application Data

(60) Provisional application No. 60/092,119, filed on Oct. 23, 1997, now abandoned.

(51) Int. Cl.[7] .................. A61K 31/58; A61K 31/56; A61P 19/00; C07J 43/00; C07J 31/00
(52) U.S. Cl. .................. 514/176; 514/178; 514/182; 540/107; 540/113; 552/523
(58) Field of Search ................. 540/107, 113; 552/523; 514/176, 178, 182

(56) References Cited

U.S. PATENT DOCUMENTS

| | | | |
|---|---|---|---|
| 2,967,188 A | 1/1961 | Dodson et al. | 260/397.4 |
| 4,659,516 A | 4/1987 | Bowler et al. | 260/397.5 |
| 4,874,754 A | 10/1989 | Nique et al. | 514/178 |
| 5,504,074 A | 4/1996 | D'Amato et al. | 514/182 |

FOREIGN PATENT DOCUMENTS

CA 2176368 5/1995

OTHER PUBLICATIONS

Longcope, C. et al., Can. J. Biochem., vol. 60, No. 2, 1982, pp. 152–156.
Anstead, G. M. et al., Steroids, vol. 62, No. 3, Mar. 1997, pp. 268–303.
Cook, C.E. et al., Life Sciences, 14, 1974, pp. 1075–1087.
Wakeling, A.E. et al., J. Ster. Biochem., 30, 1988, pp. 141–147.

*Primary Examiner*—Brenda Coleman
(74) *Attorney, Agent, or Firm*—Arnold S. Milowsky

(57) ABSTRACT

This invention provides estrogens and antiestrogens of formula I having the structure

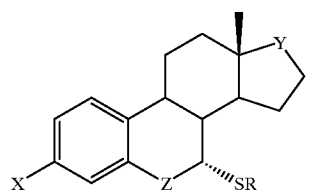

I wherein X, Y, Z, and R are as defined hereinbefore in the specification, or a pharmaceutically acceptable salt thereof.

30 Claims, No Drawings

ESTRA-1,3,5(10)-TRIENE-7α-THIOETHERS

This application claims the benefit of U.S. Provisional Application No. 60/092,119 having an effective filing date of Oct. 23, 1997 now abandoned.

BACKGROUND OF THE INVENTION

This invention provides estra-1,3,5(10)-triene-7α-thioethers which are useful as estrogenic and antiestrogenic agents.

The last decade or so, has witnessed the introduction of a new class of antiestrogenic substances devoid of any estrogenic activity. The prototypical compounds are 7α substituted steroids reported by ICI in the 1980's. (Wakeling and Bowler, J. Steroid Biochem. 30: 141–147 (1988); U.S. Pat. No. 4,659,516). Since then, there have been additional reports of steroidal compounds purported to have a purely antiestrogenic activity (See WO 93/10741 and some references contained therein). The potential advantage of these compounds is that they lack the residual agonistic properties of some mixed agonists such as tamoxifen (sold as Novadex® brand tamoxifen citrate by Zeneca Pharmaceuticals, Wilmington, Del.). The residual agonistic activity of tamoxifen can be significant in some tissues such as the uterus and the bone. While the activity in the bone may be appreciated, the estrogenic activity in the uterus may be associated with the increase in uterine cancer risk observed in longer term tamoxifen users. The pure antiestrogens reported by ICI show no trophic or proliferative activity on the uterus and would presumably not increase the risk of estrogen associated uterine cancer. Additionally, the tendency for women who are being treated chronically with tamoxifen to develop tamoxifen resistant tumors has been well documented. It is hoped that the application of antiestrogens which are devoid of any agonistic activity will be able to positively impact on tamoxifen resistant tumors by providing a more complete estrogen withdrawal from the estrogen dependent tumor types. (Wakeling, et al. J.Mol.Endocr. 2: 225–234 (1989)).

Substituents in the 7-position of estratrienes must have the a stereochemistry in order to show a good affinity for the estrogen receptor as well as good antiestrogenic efficacy (Wakeling, et al, vide supra). The prior art to date (relating to antiestrogens) on estratrienes substituted at the 7 position has been limited to side chains connected to the backbone of the steroid by carbon-carbon bonds. A 7-thiopropionate linked has been described in the literature for the purpose of conjugating to serum bovine albumins. The compound was synthesized by the radical addition of β-mercaptopropionate to 1,3,5(10),6-estratetraenes (Cook, et al Life Sci. (1974), 14 (6), 1075–1087). A series of 1,3,5(10) estratrienes wherein a broad number of claims is attached to functionality at the 7 position including thioalkyl, thioalkenyl and thioalkynyl ethers has been described with chain length up to 6 carbons. (Damato, et al, U.S. Pat. No. 5,504,074).

DESCRIPTION OF THE INVENTION

This invention provides of Formula I having the structure

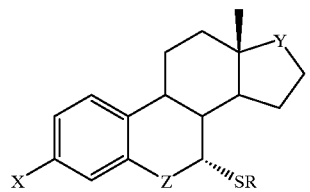

I wherein:
R is

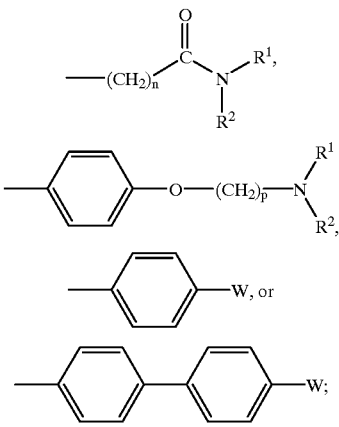

$R^1$ and $R^2$ are each, independently, alkyl of 1–6 carbon atoms, or are alkyl groups which are taken together to form a 5–7 membered saturated heterocycle;

X is hydroxy, alkoxy of 1–6 carbon atoms, or —OC(O)$R^3$;

W is

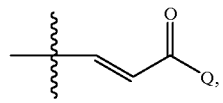

hydroxy, alkyl of 1–6 carbon atoms, halogen, —CF$_3$, alkoxy of 1–6 carbon atoms, —CHO, cyano, alkylcarbonyl of 2–7 carbon atoms, alkoxycarbonyl of 2–7 carbon atoms, amino, alkylamino of 1–6 carbon atoms, dialkylamino of 1–6 carbon atoms per alkyl group, trifluoromethoxy, hydroxyalkyl of 1–6 carbon atoms, alkoxyalkyl of 2–12 carbon atoms, —CN, —SO$_3$H, or —CO$_2$H.

$R^3$ is alkyl of 1–6 carbon atoms;

Z is

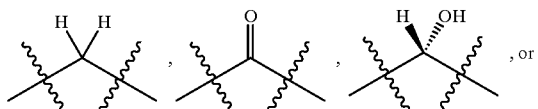

Y is

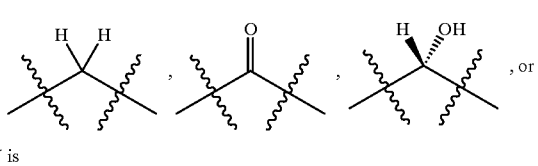

-continued

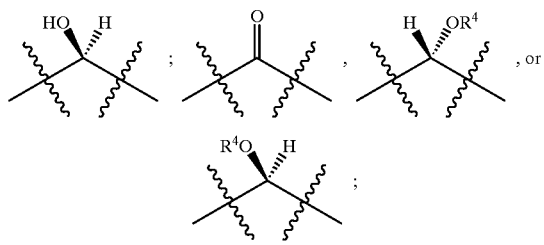

R[4] is hydrogen, alkyl of 1–6 carbon atoms, alkoyl of 2–7 carbon atoms, or benzoyl;

Q is hydrogen, —OR[5], or —NR[6]R[7];

R[5] is hydrogen or alkyl of 1–6 carbon atoms;

R[6] and R[7] are each, independently, alkyl of 1–6 carbon atoms, or are alkyl groups which are taken together to form a 5–7 membered saturated heterocycle;

n=4–12; and p=2–6;

or a pharmaceutically acceptable salt thereof which are useful as estrogenic or antiestrogenic agents.

Alkyl, and the alkyl chain of alkoxy include both straight chain as well as branched moieties. Alkoyl of 2–7 carbon atoms is defined as an alkyl carbonyl moiety in which the alkyl chain is from 1–6 carbon atoms; for example, an acetyl group. When R[4] is benzoyl the phenyl group maybe optionally mono-, di-, or tri- substituted with substituents selected from the group consisting of alkyl of 1–6 carbon atoms, alkoxy of 1–6 carbon atoms, amino, alkylamino of 1–6 carbon atoms, dialkylamino of 2–12 carbon atoms, hydroxy, halogen, cyano, —$CO_2H$, nitro, alkylcarbonyl of 2–7 carbon atoms, alkoxycarbonyl of 2–7 carbon atoms, and thiol. Halogen means bromine, chlorine, fluorine, and iodine.

The pharmaceutically acceptable salts include those derived from organic and inorganic acids such as, but not limited to: acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Carboxylate salts, preferably alkali metal salts, for example, sodium, lithium, or potassium may also be prepared as salts of carboxylic acids when a compound of this invention contains a carboxylate moiety.

Preferred compounds are those in which

Z is

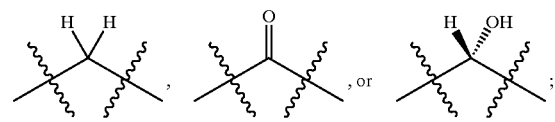

those in which:

Z is

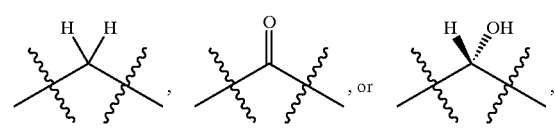

and Y is

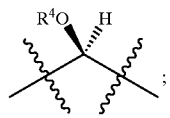

and those in which:

Z is

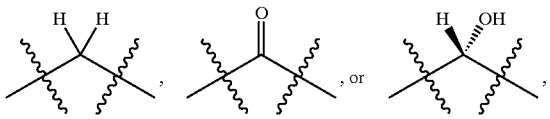

Y is

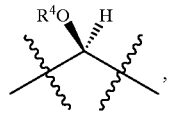

and R[4] is hydrogen or alkoyl of 2–7 carbon atoms. Compounds of this invention in which R is

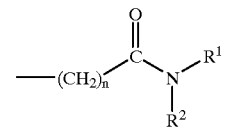

are antiestrogenic, and the compounds of this invention in which R is

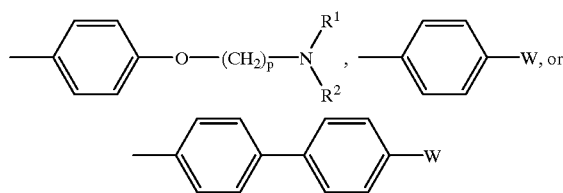

are estrogenic.

The compounds of this invention can be synthesized from 7α-bromo-3,17β-dihydroxy-estra-1,3,5(10)-trien-6-one diacetate I [CAS Registry No.97829-67-9] by the route shown in Scheme 1. Reaction of I with the appropriate thiol and sodium hydride in DMF results in substitution of the bromide which occurs with retention of the α stereochemistry at the 7-position to yield II. The acetyl group at the 3-position often comes off (at least partially) during this step. If the acetyl group is only partially removed during this step, one may desire to complete the removal by stirring the compound in methanol with potassium carbonate. The ketone II may be subsequently reduced to a 6α-hydroxy-7α-thioether III, and this reduction occurs diastereoselectively (Wintersteiner, et al, J. Org. Chem., 29, 1325 (1964); Smith, et al, J. Org. Chem., 37, 4000 (1972)). The deoxygenation is subsequently accomplished with trifluoroacetic acid and triethylsilane to give IV. The 17-β acetate may be hydrolyzed, if desired, to yield V.

Scheme 1

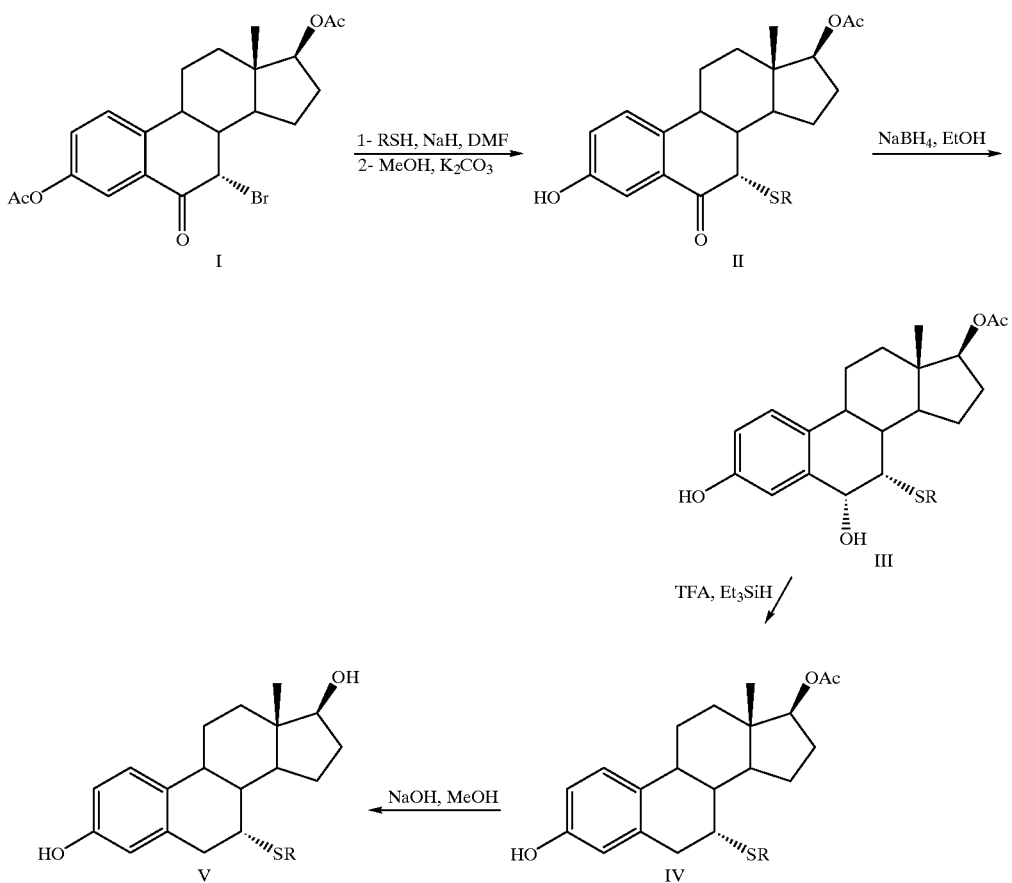

The syntheses of the cinnamamides shown in Scheme 2 are based on the same intermediate I as used for compounds of the type in Scheme 1. Displacement of the 7α-bromo substituent occurs with retention of configuration providing the desired 7α-(4'-bromophenyl) thioether VI. This reaction results in the cleavage of the labile 3-acetate. Reduction of the carbonyl group gives the 6α-hydroxy derivative VII. If the 6β-hydroxy compound is desired, one can activate the 6α-hydroxy group of VII as a mesylate and displace it with hydroxide or a suitably protected alkoxide. Alternatively, VII may be subjected to the Mitsunobu reaction (triphenylphosphine, diethylazodicarboxylate, and acetic acid) followed by hydrolysis of the intermediate 6β-acetate.

The 6α-hydroxy compound is subsequently deoxygenated with triethylsilane and trifluoroacetic acid to afford compound VIII. The bromine is replaced by the dialkyl acrylamide (or acrylate esters) using a Heck coupling reaction to give compounds of the type IX. If desired, the 17β-acetate and the acrylate ester can be hydrolyzed using NaOH/MeOH to give a 3,17β-dihydroxy estratriene X.

Scheme 2

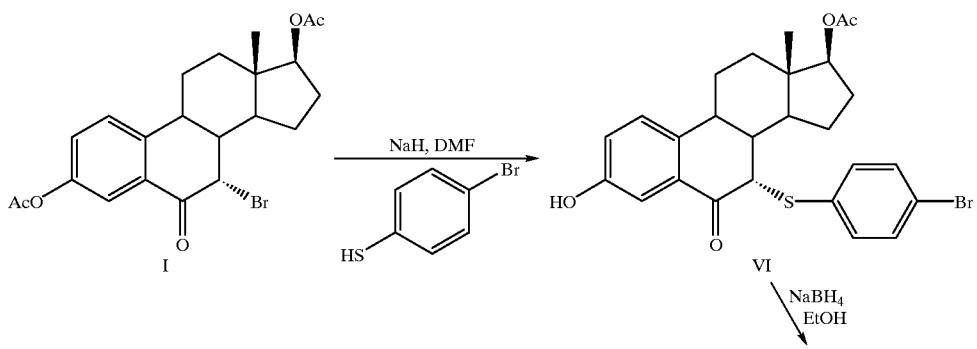

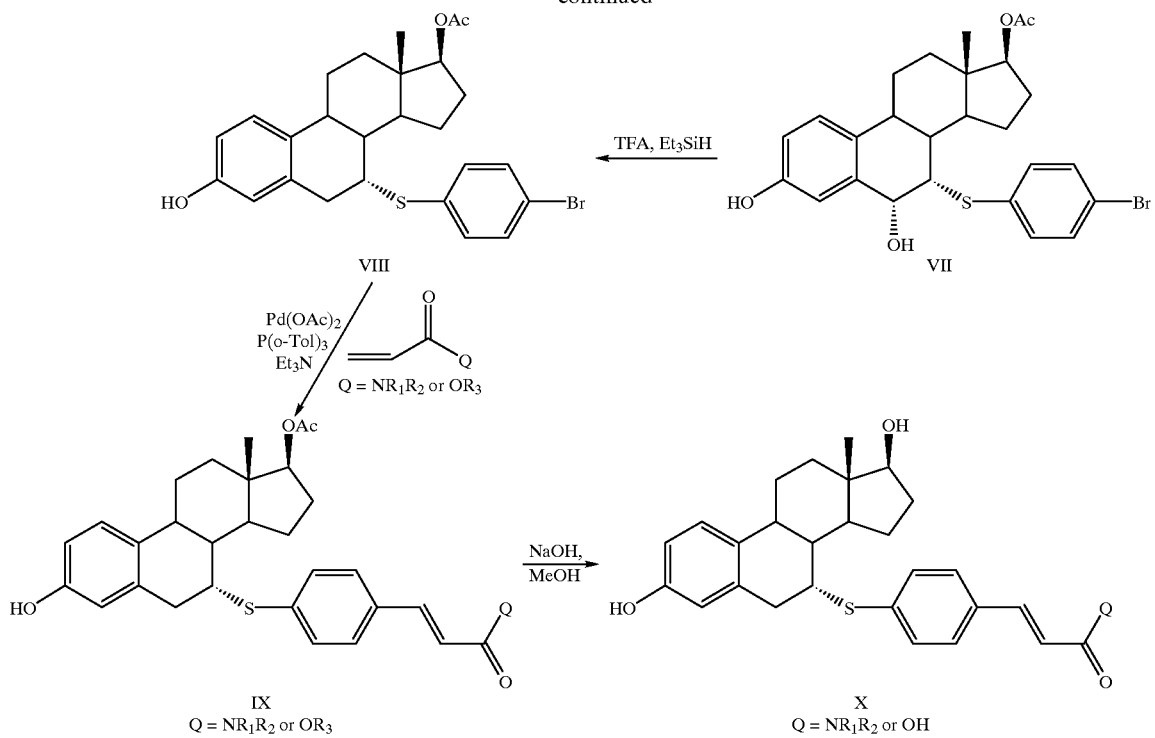

The dialkylaminoethoxy derivatives can be synthesized according to Scheme 3. The bromoketone XI [CAS Registry No; 6218-36-6] is reacted with 4-hydroxythiophenol to render XII. The ketone is reduced to give XIII and subsequently deoxygenated with TFA/Et$_3$SiH to give XIV. The free phenol is alkylated with the appropriate dialkylaminoethyl chloride to yield compounds of type XV. Protecting groups at the 17-position can be removed if desired to give compound of type XVI. The methyl ether at C-3 can be removed, if desired, through the use of reagents such as BBr$_3$, AlCl$_3$/EtSH, Pyr.HCl, etc.

Scheme 3

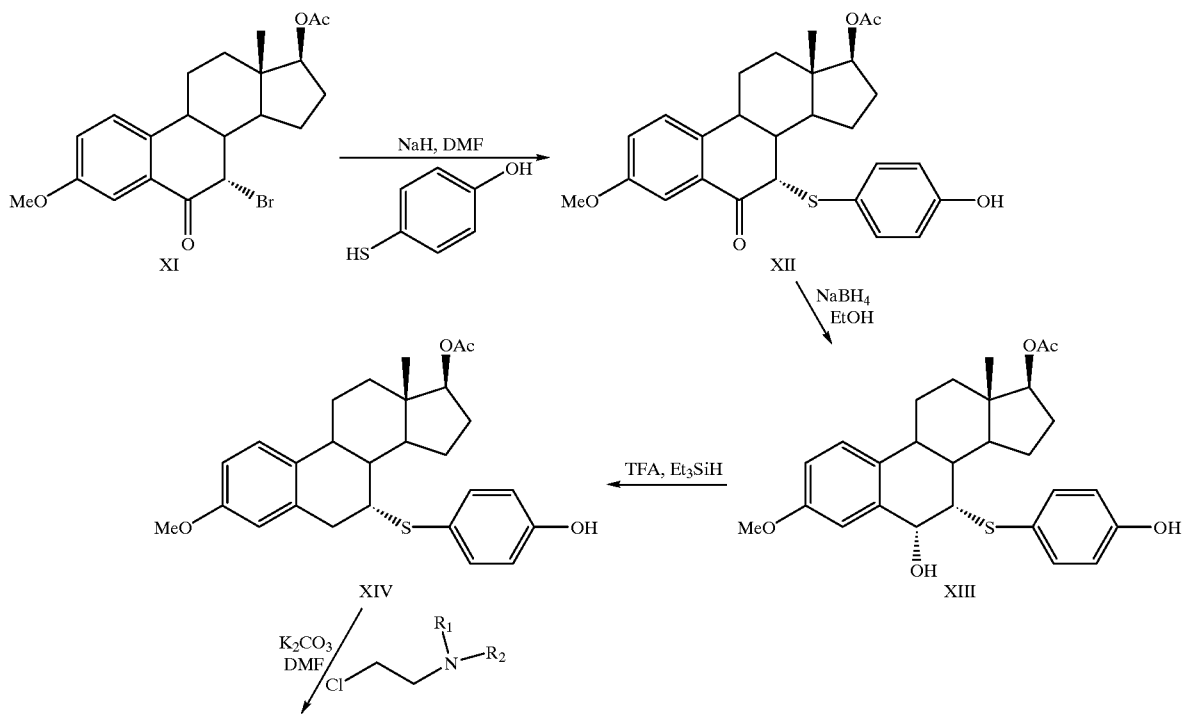

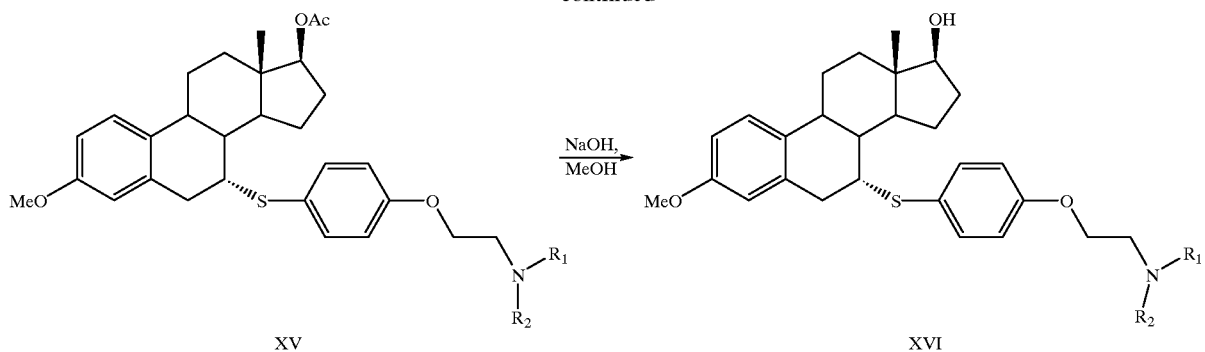

Compounds containing the biphenyl acrylate moiety are synthesized according to the process shown in Scheme 4. Compound VIII from Scheme 2 serves as the starting material for this synthesis. Suzuki coupling of VIII with 4-formylbenzeneboronic acid provides the biphenyl aldehyde XVII which can be converted to an acrylate by a Wittig reaction with the appropriate phosphonate to yield compound XVIII. Hydrolysis of the ester and simultaneous deprotection of the 17-acetate yields the acrylic acid XIX. If desired, this carboxylic acid can be converted to amides by standard coupling procedures with various amines to give compounds of type XX.

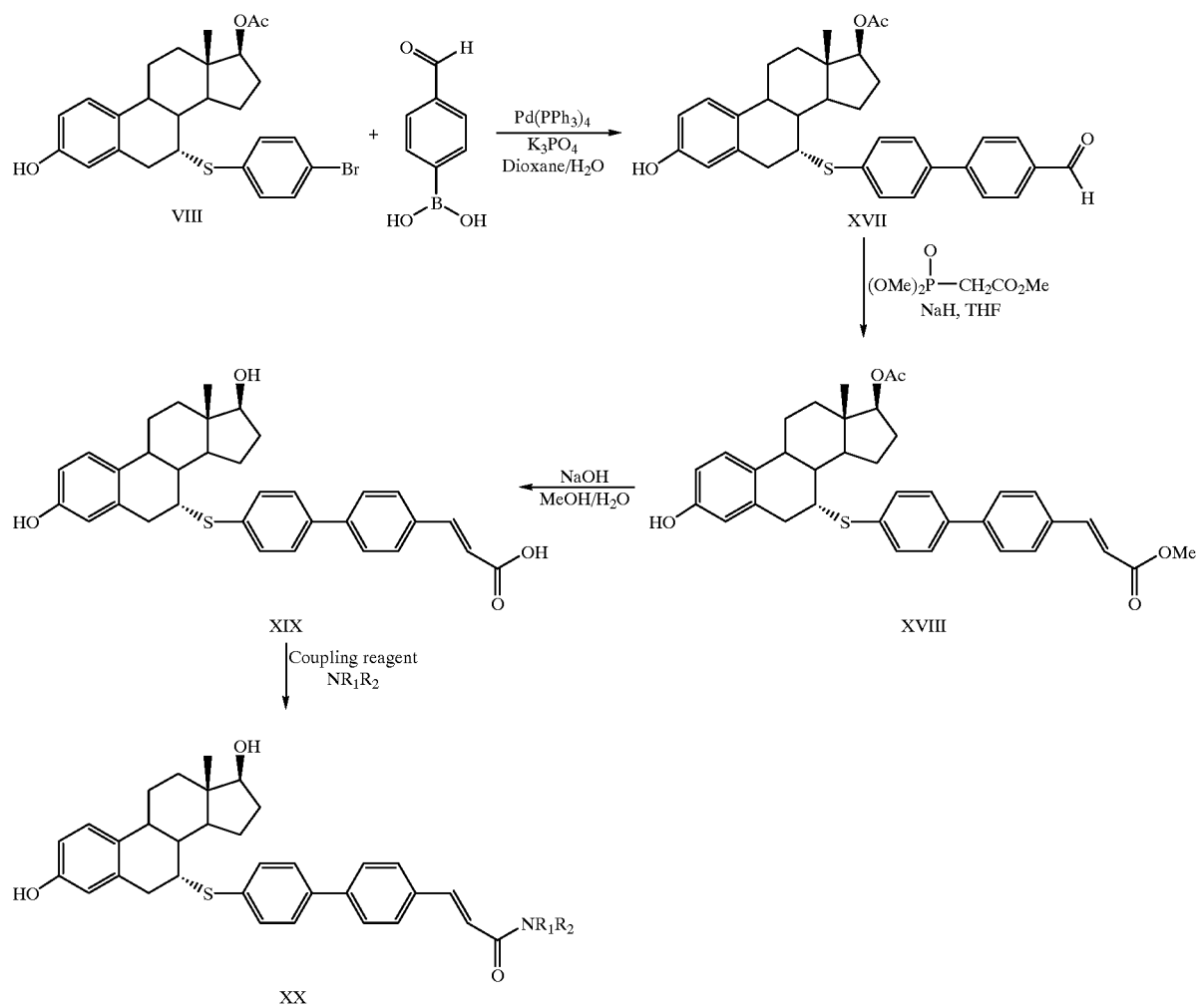

Representative compounds of this invention were evaluated in an alkaline phosphatase standard pharmacological test procedure using Ishikawa uterine cells to measure their estrogenic and antiestrogenic activity. Representative compounds were also tested for their ability to bind the human estrogen receptor. Several representative compounds were also evaluated in an in vivo standard pharmacological test procedure to determine their effect on the rat uterus. The compounds tested will be referred to by their example numbers which are given in Table 1.

TABLE 1

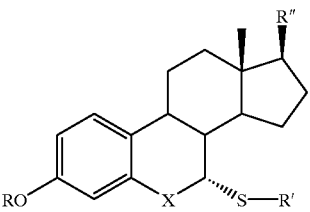

| Example # | R | X | R' | R" |
|---|---|---|---|---|
| 1 | H | C=O | —⟨C6H4⟩—OH | —OAc |
| 2 | H | C=O | —⟨C6H4⟩—OH | —OH |
| 3 | H | CH—OH | —⟨C6H4⟩—OH | —OH |
| 4 | H | CH₂ | —⟨C6H4⟩—OH | —OH |
| 5 | H | C=O | —⟨C6H4⟩—Br | —OAc |
| 6 | H | C=O | —⟨C6H4⟩—Br | —OH |
| 7 | H | CH—OH | —⟨C6H4⟩—Br | —OH |
| 8 | H | CH₂ | —⟨C6H4⟩—Br | —OH |

TABLE 1-continued
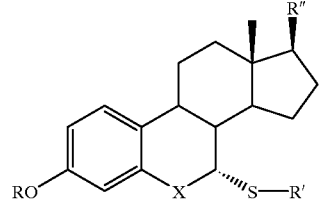
| Example # | R | X | R' | R" |
|---|---|---|---|---|
| 9 | H | CH$_2$ | 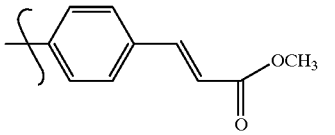 | —OAc |
| 10 | H | CH$_2$ | 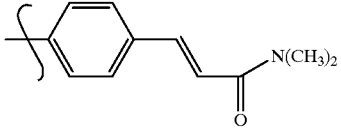 | —OH |
| 11 | H | CH$_2$ | 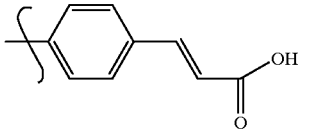 | —OH |
| 12 | H | CH$_2$ | 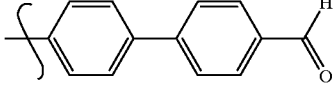 | —OH |
| 13 | H | CH$_2$ | 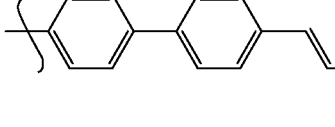 | —OH |
| 14 | CH$_3$ | CH$_2$ | 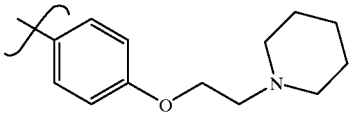 | —OAc |
| 15 | CH$_3$ | CH$_2$ | 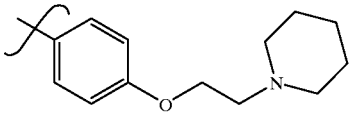 | —OH |
| 16 | H | C=O | 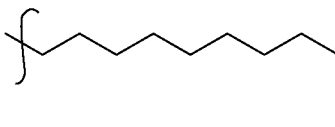 | —OH |
| 17 | H | CH—OH | 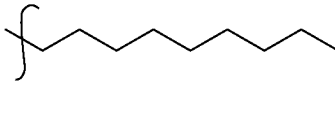 | —OH |

TABLE 1-continued

| Example # | R | X | R' | R" |
|---|---|---|---|---|
| 18 | H | CH$_2$ | ‑(CH$_2$)$_{10}$‑C(O)‑N(Me)(Bu) | —OH |

The following briefly describes the procedures used and results obtained in evaluating representative compounds of this invention.

In vitro Estrogen Receptor Binding Test Procedure

Receptor Preparation

Chinese Hamster ovary (CHO) cells overexpressing the estrogen receptor were grown in 150 mm$^2$ dishes in DMEM+10% dextran coated charcoal, stripped fetal bovine serum. The plates were washed twice with PBS and once with 10 mM Tris-HCl, pH 7.4, 1 mM EDTA. Cells were harvested by scraping the surface and then the cell suspension was placed on ice. Cells were disrupted with a hand-held motorized tissue grinder using two, 10-second bursts. The crude preparation was centrifuged at 12,000 g for 20 minutes followed by a 60 minute spin at 100,000 G to produce a ribosome free cytosol. The cytosol was then frozen and stored at −80° C. Protein concentration of the cytosol was estimated using the BCA assay with reference standard protein.

Binding Test Procedure Conditions

The competition assay was performed in a 96-well plate (polystyrene) which binds <2.0% of the total input [$^3$H]-17β-estradiol and each data point was gathered in triplicate. 100 uG/100 uL of the receptor preparation was aliquoted per well. A saturating dose of 2.5 nM [$^3$H]17β-estradiol+ competitor (or buffer) in a 50 uL volume was added in the preliminary competition when 100× and 500× competitor were evaluated, only 0.8 nM [$^3$H] 17β-estradiol was used. The plate was incubated at room temperature for 2.5 h. At the end of this incubation period 150 uL of ice-cold dextran coated charcoal (5% activated charcoal coated with 0.05% 69K dextran) was added to each well and the plate was immediately centrifuged at 99 g for 5 minutes at 4° C. 200 uL of the supernatant solution was then removed for scintillation counting. Samples were counted to 2% or 10 minutes, whichever occurs first. Because polystyrene absorbs a small amount of [$^3$H]17β-estradiol, wells containing radioactivity and cytosol, but not processed with charcoal were included to quantitate amounts of available isotope. Also, wells containing radioactivity but no cytosol were processed with charcoal to estimate unremovable DPM of [$^3$H] 17β-estradiol. 96-well plates were used because they have proven to bind the least amount of estradiol.

Analysis of Results

Counts per minute (CPM) of radioactivity were automatically converted to disintegrated per minute (DPM) by the Beckman LS 7500 Scintillation Counter using a set of quenched standards to generate a H# for each sample. To calculate the % of estradiol binding in the presence of 100 or 500 fold competitor the following formula was applied:

((DPM sample−DPM not removed by charcoal/(DPM estradiol−DPM not removed by charcoal))×100%=% of estradiol binding For the generation of IC$_{50}$ curves, % binding is plotted vs compound. IC$_{50}$'s are generated for compounds that show >30% competition at 500× competitor concentration. Values are reported as IC$_{50}$ values. For comparison, 17β-estradiol has displayed IC$_{50}$'s from $10^{-8}$–$10^{-9}$. For a description of these methods, see Hulme, E. C., ed. 1992. Receptor-Ligand Interactions: A Practical Approach. IRL Press, New York. (see especially chapter 8).

Ishikawa Cell Alkaline Phosphatase Test Procedure

Cell Maintenance and Treatment

Ishikawa cells were maintained in DMEM/F12 (50%:50%) containing phenol red+10% fetal bovine serum and the medium was supplemented with 2 mM Glutamax, 1% Pen/Strap and 1 mM sodium pyruvate. Five days prior to the beginning of each evaluation (treatment of cells) the medium was changed to phenol red-free DMEM/F12+10% dextran coated charcoal stripped serum. On the day before treatment, cells were harvested using 0.5% trypsin/EDTA and plated at a density of 5×10$^4$ cells/well in 96-well tissue culture plates. Test compounds were dosed at $10^{-6}$, $10^{-7}$ and $10^{-8}$M in addition to $10^{-6}$ M (compound)+$10^{-9}$ M 17β-estradiol to evaluate the ability of the compounds to function as antiestrogens. Cells were treated for 48 h prior to assay. Each 96-well plate contained a 17β-estradiol control. Sample population for at each dose was n=8.

Alkaline Phosphatase Test Procedure

At the end of 48 h the media was aspirated and cells were washed three times with phosphate buffered saline (PBS); 50 μL of lysis buffer (0.1 M Tris-HCl, pH 9.8, 0.2% Triton X-100) was added to each well. Plates were placed at −80° C. for a minimum of 15 minutes. Plates were thawed at 37° C. followed by the addition of 150 μL of 0.1 M Tris-HCl, pH 9.8, containing 4 mM para-nitrophenylphosphate (pNPP) to each well (final concentration, 3 mM pNPP).

Absorbance and slope calculations were made using the KineticCalc Application program (Bio-Tek Instruments, Inc., Winooski, Vt.). Results are expressed as the mean +/−S.D. of the rate of enzyme reaction (slope) averaged over the linear portion of the kinetic reaction curve (optical density readings every 5 minutes for 30 minutes absorbance reading). Results for compounds are summarized as percent of response related to 1 nM 17β-estradiol.

Representative compounds of this invention were evaluated for estrogenic activity by the alkaline phosphatase method and corresponding $ED_{50}$ values (95% C.I.) were calculated. The four compounds were used as reference standards:

17β-estradiol 0.03 nM
17α-estradiol 1.42 nM
estriol 0.13 nM
estrone 0.36 nM

A description of these methods is described by Holinka, C. F., Hata, H., Kuramoto, H. and Gurpide, E. (1986) Effects of steroid hormones and antisteroids on alkaline phosphatase activity in human endometrial cancer cells (Ishikawa Line). Cancer Research, 46:2771–2774, and by Littlefield, B. A., Gurpide, E., Markiewicz, L., McKinley, B. and Hochberg, R. B. (1990) A simple and sensitive microtiter plate estrogen bioassay based on stimulation alkaline phosphatase in Ishikawa cells; Estrogen action of D5 adrenal steroids. Endocrinology, 6:2757–2762.

Rat Uterotrophic/Antiuterotrophic Test Procedure

The estrogenic and antiestrogenic properties of the compounds were determined in a 4-day immature rat uterotrophic assay (as described previously by L. J. Black and R. L. Goode, Life Sciences, 26, 1453 (1980)). Immature Sprague-Dawley rats (female, 18 days old) were tested in groups of six. The animals were treated by daily ip injection with 10 ug compound, 100 ug compound, (100 ug compound+1 uG 17β-estradiol for compounds which were strong antiestrogens in alkaline phoshatase assay) to check antiestrogenicity, and 1 ug 17β-estradiol, with 50% DMSO/50% saline as the injection vehicle. On day 4 the animals were sacrificed by $CO_2$ asphyxiation and their uteri were removed and stripped of excess lipid, any fluid removed and the wet weight determined. A small section of one horn was submitted for histology and the remainder used to isolate total RNA in order to evaluate complement component 3 gene expression.

Results

The following tables and description describes the results obtained in the standard pharmaceutical test procedures.

TABLE 2

Ishikawa Cell Alkaline Phosphatase Assay
Example Concentrations

| Example # | 1 uM | 0.1 uM | 0.01 uM | 1 uM + 1 nM $E_2$ |
| --- | --- | --- | --- | --- |
| 1 | 29% | 9% | 7% | 76% |
| 2 | 42% | 14% | 7% | 87% |
| 3 | 75% | 88% | 86% | 97% |
| 4 | 57% | 47% | 7% | 6% |
| 5 | 104% | 108% | 58% | 106% |
| 6 | 104% | 100% | 31% | 109% |
| 7 | 66% | 58% | 46% | 98% |
| 8 | 92% | 59% | 29% | 95% |
| 9 | 61% | 33% | 1% | 59% |
| 10 | 28% | 12% | 0% | 57% |
| 11 | 21% | 23% | 0% | 50% |
| 12 | 89% | 67% | 17% | 92% |
| 13 | 95% | 72% | 11% | 101% |
| 14 | 39% | 3% | 2% | 105% |
| 15 | 22% | 0% | 0% | 69% |
| 16 | 42% | 22% | 7% | 66% |
| 17 | 1% | 0% | 0% | 28% |
| 18 | 0% | 0% | 0% | 1% |

Compounds which display low percentages in the agonist mode, as well as low percentages in the antagonist modes (#17 and #18, especially) are behaving as pure estrogen antagonists in this uterine cell line. Compounds that display intermediate values in the agonist and antagonist modes (#9–#11) are behaving as mixed agonists, thus having characteristics of estrogens with partial efficacy and as antiestrogens with partial efficacy. Compounds which show full efficacy (100%) for at least the higher doses (#5 and #6) and do not antagonize a co-administered dose of estradiol are considered to be fully efficacious agonists in this uterine cell line.

Compounds were tested for their ability to displace estradiol in a human ER-receptor preparation as described above. $IC_{50}$'s were derived for the competition curves and this is the number reported in Table 3. 17β-estradiol has $IC_{50}$'s ranging from $10^{-8}$–$10^{-9}$ M.

TABLE 3

ER Receptor $IC_{50}$'s for Examples #1–#18

| Example # | Receptor $IC_{50}$ (uM) |
| --- | --- |
| 1 | No Binding |
| 2 | 2.5 |
| 3 | 0.01 |
| 4 | 0.3 |
| 5 | No Binding |
| 6 | 1.5 |
| 7 | 0.8 |
| 8 | 0.8 |
| 9 | No Binding |
| 10 | N/A |
| 11 | 1.5 |
| 12 | 0.3 |
| 13 | 0.4 |
| 14 | No Binding |
| 15 | 11 |
| 16 | 0.3 |
| 17 | 0.4 |
| 18 | 0.1 |

As might be anticipated, compounds which had an acetate in the 17β-position competed less effectively for the human estrogen receptor (compounds #1, #5, #9, and #14). Some of these compounds did, however, have activity in the Ishikawa cells, probably indicating the ability of these cells to partially metabolize these compounds by enzymatic hydrolysis of the 17β-acetate.

Representative compounds of this invention were evaluated in the rat uterotrophic/antiuterotrophic assay to determine their in vivo effects on the rat uterus. Examples #3 and #18 were tested in both the agonist mode as well as the antagonist mode (cmpd+17β-estradiol). The results are given in Table 4 for selected examples.

TABLE 4

Effect on Rat Uterus

| Example # | Control | 1 ug 17β | 1 ug Cpd | 100 ug Cpd | 1 ug $E_2$ + 100 ug Cpd |
| --- | --- | --- | --- | --- | --- |
| 2 | 30.5 mg | 83.8 mg | 39.4 mg | 83.1 mg | N/A |
| 3 | 42.0 mg | 94.6 mg | 62.4 mg | 99.9 mg | 106.1 mg |
| 4 | 42.0 mg | 94.6 mg | 37.9 mg | 45.4 mg | N/A |
| 6 | 38.8 mg | 87.6 mg | 29.0 mg | 97.7 mg | N/A |
| 8 | 38.8 mg | 87.6 mg | 35.8 mg | 64.7 mg | N/A |
| 13 | 43.1 mg | 82.1 mg | 48.0 mg | 55.8 mg | N/A |
| 16 | 39.5 mg | 92.6 mg | 41.3 mg | 72.5 mg | N/A |
| 17 | 39.5 mg | 92.6 mg | 36.5 mg | 64.2 mg | N/A |
| 18 | 43.1 mg | 82.1 mg | 31.8 mg | 41.6 mg | 46.0 mg |

As can be seen from Table 4, some of the compounds functioned as full agonists giving uterine stimulatory effects similar to 17β-estradiol, whereas other compounds showed no uterine effects by themselves. Compound #18 was a very efficacious antagonist, having no uterine effects when dosed alone or with a co-administered dose of 17β-estradiol.

Based on the results obtained in the standard pharmacological test procedures, compounds of this invention in which R is

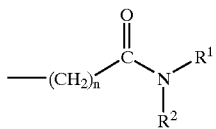

are antiestrogenic, and the compounds of this invention in which R is

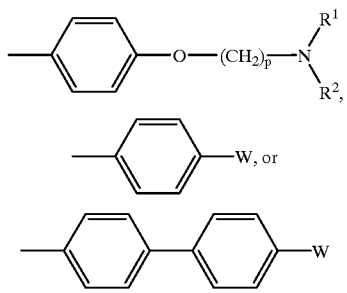

are estrogenic.

Compounds of this invention which are estrogenic are useful in treating or preventing in a mammal disease states or syndromes which are caused or associated with an estrogen deficiency (in certain tissues such as bone or cardiovascular) or an excess of estrogen (in the uterus or mammary glands). The pure estrogen antagonists can completely antagonize the trophic effects of estrogen agonists in uterine tissue and are useful in the treatment or diseases or disorders which result from proliferation or abnormal development, actions or growth of endometrial or endometrial-like tissues.

Based on the results obtained in the standard pharmacological test procedures, the estrogenic compounds of this invention are useful in treating diseases or conditions which result from estrogen effects and estrogen excess or deficiency including osteoporosis, prostatic hypertrophy, vaginal and skin atrophy, acne, cardiovascular disease, contraception, Alzheimer's disease, cognitive decline and other CNS disorders. Additionally, the estrogneic compounds of this invention can be used for contraception in pre-menopausal women, as well as hormone replacement therapy in post-menopausal women or in other estrogen deficiency states where estrogen supplementation would be beneficial.

The estrogenic compounds of this invention are also useful in the treatment for and inhibition of bone loss, which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatments for osteoarthritis, hypocalcemia, hypercalcemia, Paget's disease, osteomalacia, osteohalisteresis, multiple myeloma and other forms of cancer having deleterious effects on bone tissues.

Based on the results obtained in the standard pharmacological test procedures, the compounds of this invention which are estrogen antagonists are useful in providing antiestrogen therapy, particularly in treating male pattern baldness, dysfunctional uterine bleeding, endometrial polyps, benign breast disease, uterine leiomyomas, adenomyosis, in treating neoplasms such as ovarian cancer, breast cancer, endometrial cancer, melanoma, prostrate cancer, cancers of the colon, and CNS cancers, in treating endometriosis, polycystic ovary syndrome, and infertiltiy, and in providing. The estrogen antagonists of this invention are also useful in disease states where amenorrhea is advantageous, such as leukemia, endometrial ablations, chronic renal or hepatic disease or coagulation diseases or disorders.

Effective administration of these compounds may be given at a dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermeally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgement of the medical practitioner involved. It is preferred that the administration of one or more of the compounds herein begin at a low dose and be increased until the desired effects are achieved.

The following procedures describe the preparation of representative examples of this invention. The term compound is used when describing compounds from the text (compounds are associated with roman numeral numbering). The term example, refers to specific examples listed in table 1.

All reactions were carried out under a nitrogen atmosphere. Chromatography was performed using 230–400 mesh silica gel. Thin layer chromatography was performed with Silica Gel 60 $F_{254}$ plates. $^1$H NMR spectra were obtained on a Bruker AM-400 instrument in DMSO-$d_6$ or CDCl$_3$ and chemical shifts reported in ppm.

General Procedure 1: Substitution of 6-oxo-7-bromo Estradiol Diacetate with Thiol Nucleophiles to Form Compounds of Type II from Scheme 1

A solution of an alkanethiol or benzenethiol (2–2.5 equivalents) in DMF was cooled to 0° C. and treated with 2–2.5 equivalents of NaH (60% dispersion in mineral oil). The reaction mixture was stirred a few minutes, then the bromo-ketone I (Scheme 1) (1 equivalent) dissolved in DME and added. The reaction mixture was allowed to slowly come to rt, stirred overnight, poured into 0.1 N HCl$_{aq.}$ and extracted with ethyl ether. The ether extract was washed with NaHCO$_{3\ aq.}$, brine, and then dried over sodium sulfate. The filtrate was concentrated and the residue chromatographed on silica gel to yield the product, usually in greater then 50% yield. Displacement of the bromo-substituent proceeds with retention of the stereochemistry (diastereoselectivity >95%) as determined by $^1$H NMR spectroscopy. The signal for the 7-proton displays a very small coupling constant (<3.5 Hz) with the 8β-proton, therefore, the 7-hydrogen was equatorial (β). The 3-O-acetyl group may be hydrolyzed or partially hydrolyzed during the course of the reaction. If incomplete cleavage occurs as evaluated by TLC analysis (EtOAc/hexanes), the crude mixture (material after workup but before chromatography or crystallization) may be dissolved in methanol and treated with an equivalent of K$_2$CO$_3$. This will convert the material to completely deacetylated material. Alternatively, if desired, the compound may be reacetylated at this point by taking the crude reaction mixture in pyridine and treating with an excess of acetic anhydride and stirring until complete reaction occurs. The reaction may be warmed to accelerate the process. Reacetylation is not necessary, however, to proceed with the synthesis since the phenolic group does not interfere with any of the subsequent steps.

General Procedure 2: Reduction of 6-oxo-7-thioether Estratrienes to 6-hydroxy-7-thioether Estratrienes (Compound III from Scheme 1)

The 6-oxo-7-thio estrogen II (Scheme 1) from the previous step was dissolved in EtOH and an excess of NaBH$_4$ was added. The reaction was followed by TLC until complete (typically several hours). The reaction was worked up by adding a saturated solution of aqueous ammonium chloride and evaporating most of the ethanol on a rotary evaporator. The aqueous portion was then extracted with ethyl acetate, washed with water, brine, dried over sodium sulfate and concentrated. Typically, this reaction is very clean and the compound can be taken to the next step without further purification. If desired, however, the reaction mixture may be chromatographed on silica gel using ethyl acetate/hexanes for the eluting solvents.

General Procedure 3: Deoxygenation of the 6-hydroxy Functionality and 17-acetate Hydrolysis to Form Compounds of Structure Type IV and V from Scheme 1

1.25 grams of 6-hydroxy-7-thioether estratriene III (Scheme 1) from the immediately previous step was dissolved in 12 mL of acetonitrile, to which was added 14 mL of Et$_3$SiH and 34 mL of CF$_3$COOH. The reaction was heated to approximately 50° C. from several hours to overnight. After TLC indicates that the reaction was complete, reaction mixture was diluted with ether and washed several times with a saturated aqueous solution of sodium bicarbonate. The ether was then washed with water, brine and dried over sodium sulfate. After concentration, the residue can be chromatographed on silica gel (typically with ethyl acetate/hexanes mixtures). If desired, the acetate at the 17-position can be easily saponified by dissolving the acetate in methanol and adding an aqueous NaOH solution. The reaction was monitored by TLC for the disappearance of starting materials. If several equivalents of NaOH were used, the reaction was finished in approximately one hour. The reaction was subsequently neutralized with aqueous HCl solution and the methanol stripped off. The product was extracted with ethyl acetate or ether and washed with aqueous NaHCO$_3$ solution, water, brine and dried over sodium sulfate. If necessary, the material can be chromatographed on silica gel.

General Procedure 4: Heck Coupling Reaction for the Synthesis of Acrylates or Acrylamides from Schemes 2 and 4

Compounds analogous to VIII (Scheme 2) or #8 from Table 1 were used as the starting material for the synthesis of compounds #9, #10, and #11 (Table 1). Starting material was taken up in triethylamine and purged with nitrogen. The resulting solution was treated with 1 mole % Pd(OAc)$_2$ and 4 mole % tri-orthotolylphosphine and 1.25 to 1.50 equivalents of the appropriate acrylate or acrylamide. The reactions were typically run in capped pressure tubes under in oxygen free environment. The reaction was heated at 100–120° C. for from several hours to several days depending on the specific substrate and acrylate or acrylamide used. The reaction can be accelerated by using a greater amount of catalyst (up to 5 mole % of the Pd(OAc)$_2$). When the reaction was complete by TLC analysis, the solution was concentrated and partitioned between 2 N HCl aq and ethyl ether. The ether layer was washed with NaHCO$_3$ aq., brine, and dried over sodium sulfate. Concentration and chromatography provides the desired compounds in yields generally >50%. If an acrylic acid like compound #11 (Table 1) is desired, then hydrolysis of the methyl acrylate #9 (Table 1) can easily be accomplished in good yield by base saponification in MeOH/THF 2.5 N NaOH aq. (8:15:2 v/v/v) at room temperature overnight. The acetate at C-17 (if present) is also cleaved during this reaction. The reaction was worked up by adding a 2 N HCl aq. solution to acidify and evaporating off the MeOH and THF. The resultant was extracted with ether and washed with water, brine, and dried over sodium sulfate. The residue can then be chromatographed on silica gel (MeOH/CH$_2$Cl$_2$) to yield the pure product in good yields.

General Procedure 5: Synthesis of Compounds Containing the Basic Side Chain from Scheme 3

Compounds #14 and #15 (Table 1) can be readily synthesized from precursor compounds analogous to the 3-methyl ether-17β acetate estratriene XIV (Scheme 3). The starting material was dissolved in DMF and treated with 3 equivalents of K$_2$CO$_3$ and 1.5 equivalents of the appropriate chloroethylamine hydrochloride salt and the reaction heated at 50° C. for overnight. The reaction was worked up by partitioning between water and ether, and the ether layer was washed with brine, and then dried over sodium sulfate. The ether was concentrated and the residue chromatographed on silica gel using ethyl acetate. If the compound without an acetate at the 17-position is desired (like compound #15 (Table 1) then base saponification can be easily accomplished by dissolving the substrate in a solution of MeOH/THF/2.5 N NaOH (1:1:1) and stirring at rt until the reaction was complete by TLC. Reaction mixtures are partitioned between ether and water and the ether layer washed with brine and dried over sodium sulfate. The ether is then concentrated and the residue chromatographed on silica gel ($CH_2Cl_2$/MeOH) to yield compounds #14 or #15 (Table 1).

General Procedure 6: Synthesis of Biphenyl Analogues from Scheme 4

Compounds #12 and #13 (Table 1) can be prepared using a compound analogous to #8 (Table 1) or compound VIII (scheme 4) as a precursor. The precursor was dissolved in a solution of dioxane/water (3:1) and treated with 1.5 equivalents of 4-formylbenzeneboronic acid and 1.5 equivalents of $K_3PO_4$. The reaction mixture was purged with nitrogen and 5 mole % of $Pd(PPh_3)_4$ added and the reaction heated under reflux from several hours to overnight. The solution was concentrated and the reaction mixture partitioned between ether and water and the aqueous layer acidified with 1 N HCl. The ether layer was washed with water and brine, and dried over sodium sulfate and concentrated. Chromatography on silica gel (EtOAc/hexanes) yields the pure, desired compound. In order to make the acrylate, 1.5 equivalents of $(CH_3O)_2P(O)CH_2CO_2CH_3$ was dissolved in THF and treated with 1.5 equivalents of NaH (60% dispersion in mineral oil) at 0° C. The starting material, dissolved in THF, was added by syringe to the reaction at 0° C. After just several minutes, the reaction was complete by TLC analysis. Work-up was accomplished by adding aqueous ammonium chloride solution and removing the THF under reduced pressure. The resultant solution was extracted with ether and washed with water, brine, and dried over magnesium sulfate, concentrated, and chromatographed on silica gel (EtOAc:hexanes) to yield the desired products in good yield. If the acrylic acid was desired, then the ester can be hydrolyzed with 1 N KOHaq./MeOH/THF (3:2:6) at room temperature (typically takes at least 24 hours). Work-up was accomplished by acidifying the reaction with 2 N HCl and removing the organics under reduced pressure. Ether was added, and the ether layer was washed with water, brine, and dried over $MgSO_4$. The reaction mixture was concentrated and chromatographed using $MeOH/CH_2Cl_2$/0.5%$CH_3COOH$ to yield the desired acrylic acid. Alternatively, washing with $NaHCO_3$ aq., provides the sodium salt (example #13 used as sodium salt of the carboxylic acid).

General Procedure 7: Preparation of Undecamide Analogues like Examples #16, #17, and #18

These compounds were made according to the same general procedure as that given for the phenylthio compounds (the first three general procedures listed in this section). The only difference was the side chain utilized. The thio-alkylamide side chains were synthesized according to standard procedures (Labrie, et al. J. Med. Chem. 1994, 37, 1115–1125) and were used in the same manner as the thiophenols in the first general procedure.

EXAMPLE 1

(7α,17β) 17-Acetoxy-3-hydroxy-7-(4-hydroxyphenyl)thio-estra-1,3,5(10)-triene-6-one Prepared by General Procedure 2

M.p. 150–155° C.; $^1$H NMR (DMSO) 9.74 (s, 1 H), 9.65 (s, 1 H), 7.31 (d, 1 H, J=8.6 Hz), 7.28 (d, 1 H, J=2.9 Hz), 7.18 (d, 2 H, J=8.8 Hz), 7.00 (dd, 1 H, J=8.6 Hz, 2.9 Hz), 6.72 (d, 2 H, J=8.6 Hz), 4.68 (t, 1 H, J=8.6 Hz), 3.48 (d, 1 H, J=3.1 Hz), 2.72–2.62 (m, 1 H), 2.42–2.33 (m, 1 H), 2.29 (dt, 1 H, J=11.0 Hz, 3.1 Hz), 2.20–2.14 (m, 1 H), 2.01 (s, 3 H), 1.96–1.89 (m, 1 H), 1.79–1.68 (m, 2 H), 1.58–1.30 (m, 4 H), 0.79 (s, 3 H); IR (KBr) 3300 br, 2890, 1735, 1660 $cm^{-1}$; MS(EI) m/z 452 (M+).

EXAMPLE 2

(7α,17β) 3,17-Dihydroxy-7-(4-hydroxyphenyl)thio-estra-1,3,5(10)-triene-6-one

Prepared by General Procedure 2

M.p. 120–124° C.; $^1$H NMR (DMSO) 9.73 (s, 1 H), 9.64 (s, 1 H), 7.31 (d, 1 H, J=8.6 Hz), 7.27 (d, 1 H, J=2.9 Hz), 7.15 (d, 2 H, J=8.6 Hz), 6.99 (dd, 1 H, J=8.3 Hz, 2.9 Hz), 6.72 (d, 2 H, J=8.8 Hz), 4.59 (d, 1 H, J=4.8 Hz), 3.63–3.58 (m, 1 H), 3.46 (d, 1 H, J=3.1 Hz), 2.64 (dt, 1 H, J=10.3 Hz, 3.3 Hz), 2.44–2.35 (m, 1 H), 2.21 (dt, 1 H, J=10.5 Hz, 2.9 Hz), 2.00–1.86 (m, 1 H), 1.82–1.62 (m, 3 H), 1.46–1.20 (m, 4 H), 0.67 (s, 3 H); IR (KBr) 3450 br, 2950, 1660 cm–1; MS(EI) m/z 410 (M+).

EXAMPLE 3

(6α,7α,17β) 7-(4-Hydroxyphenyl)thio-estra-1,3,5(10)-triene-3,6,17-triol

Prepared by General Procedure 2

M.p. 220–225° C.; $^1$H NMR (DMSO) 9.50 (s, 1 H), 9.09 (s, 1 H), 7.37 (d, 2 H, J=8.6 Hz), 7.02 (d, 1 H, J=8.6 Hz), 6.97 (d, 1 H, J=2.2 Hz), 6.68 (d, 2 H, J=8.8 Hz), 6.55 (dd, 1 H, J=8.3 Hz, 2.6 Hz), 5.18 (d, 1 H, J=7.9 Hz), 4.82 (dd, 1 H, J=6.2 Hz, 4.8 Hz), 4.49 (d, 1 H, J=4.8 Hz), 3.56–3.49 (m, 1 H), 3.24 (dd, 1 H, J=4.4 Hz, 1.54 Hz), 2.56–2.50 (m, 1 H), 2.28–2.20 (m, 1 H), 1.85–1.70 (m, 3 H), 1.63 (q, 1 H, J=9.4 Hz), 1.34–1.10 (m, 5 H), 0.65 (s, 3 H); IR (KBr) 3400 br, 2900 cm–1; MS(EI) m/z 412 ($M^+$).

EXAMPLE 4

(7α,17β) 7-(4-Hydroxyphenyl)thio-estra-1,3,5(10)-triene-3,17-diol

Prepared by General Procedure 3

M.p. 140–145° C.; $^1$H NMR (DMSO) 9.62 (s, 1 H), 9.04 (s, 1 H), 7.19 (d, 2 H, J=8.6 Hz), 7.08 (d, 1 H, J=8.6 Hz), 6.73 (d, 2 H, J=8.6 Hz), 6.54 (dd, 1 H, J=8.3 Hz, 2.4 Hz), 6.38 (d, 1 H, J=2.4 Hz), 4.52 (d, 1 H, J=4.8 Hz), 3.58–3.52 (m, 1 H), 3.31–3.28 (m, 1 H), 3.02 (dd, 1 H, J=16.7 Hz, 3.7 Hz), 2.72 (d, 1 H, J=16.7 Hz), 2.40–2.25 (m, 2 H), 1.94–1.84 (m, 1 H), 1.82–1.71 (m, 2 H), 1.62–1.45 (m, 2 H), 1.41–1.10 (m, 4 H), 0.66 (s, 3 H); IR (KBr) 3390, 2900, 1600 $cm^{-1}$; MS(EI) m/z 396 ($M^+$).

EXAMPLE 5

(7α,17β) 17-Acetoxy-7-(4-bromophenyl)thio-3-hydroxy-estra-1,3,5(10)-trien-6-one

Prepared by General Procedure 2

M.p. 190–192° C.; $^1$H NMR ($CDCl_3$) 7.50 (d, 1 H, J=3.1 Hz), 7.42 (d, 2 H, J=8.8 Hz), 7.33–7.31(1 H+d, 2 H, J=8.8 Hz), 7.07 (dd, 1 H, J=8.6 Hz, 3.1 Hz), 5.07 (s, 1 H), 4.79 (dd, 1 H, J=9.0 Hz, 8.1 Hz), 3.75 (d, 1 H, J=3.1 Hz), 2.88–2.80 (m, 1 H), 2.45–2.39 (m, 1 H), 2.33 (dt, 1 H, J=10.8 Hz, 3.3 Hz), 2.36–2.26 (m, 1 H), 2.08 (s, 3 H), 2.05–1.90 (m, 2 H), 1.85–1.75 (m, 1 H), 1.65–1.38 (m, 4 H), 0.86 (s, 3 H); IR (KBr) 3250 br, 2900, 1720, 1650 $cm^{-1}$; MS(EI) m/z 516, 514 (M+, bromine Isotopes).

EXAMPLE 6

(7α,17β) 7-(4-Bromophenyl)thio-3,17-dihydroxy-
estra-1,3,5(10)-trien-6-one

Prepared by General Procedure 2

M.p. 190–194° C.; $^1$H NMR (DMSO) 9.67 (s, 1 H), 7.52 (d, 2 H, J=8.6 Hz), 7.36 (d, 2 H, J=8.6Hz), 7.33 (d, 1 H, J=8.4Hz), 7.25 (d, 1 H, J=2.9 Hz), 7.01 (dd, 1 H, J=8.6 Hz, 2.9 Hz), 4.60 (d, 1 H, J=4.8 Hz), 3.78 (d, 1 H, J=3.3 Hz), 3.61–3.56 (m, 1 H), 2.62 (dt, 1 H, J=11.0 Hz, 4.2 Hz), 2.44–2.38 (m, 1 H), 2.31 (dt, 1 H, J=11.0 Hz, 3.5 Hz), 1.96–1.82 (m, 2 H), 1.76–1.68 (m, 1 H), 1.64–1.56 (m, 1 H), 1.42–1.20 (m, 4 H), 0.68 (s, 3 H); IR (KBr) 3410 br, 2900, 1660 cm-1; MS(EI) m/z 474, 472 (M+, bromine Isotopes).

EXAMPLE 7

(6α,7α,17β) 7-(4-Bromophenyl)thio-estra-1,3,5(10)-
triene-3,6,17-triol

Prepared by General Procedure 2

M.p. 140–145° C.; $^1$H NMR (DMSO) 9.11 (s, 1 H), 7.45 (s, 4 H), 7.04 (d, 1 H, J=8.6 Hz), 6.96 (d, 1 H, J=2.6 Hz), 6.56 (dd, 1 H, J=8.6 Hz, 2.6 Hz), 5.43 (d, 1 H, J=7.5 Hz), 4.94–4.91 (m, 1 H), 3.55–3.48 (m, 2 H), 2.50–2.48 (m, 1 H), 2.28–2.24 (m, 1 H), 1.95–1.90 (m, 1 H), 1.82–1.71 (m, 2 H), 1.62–1.53 (m, 1 H), 1.32–1.10 (m, 5 H), 0.67 (s, 3 H); IR (KBr) 3400 br, 2910 cm$^{-1}$; MS(eI) m/z 476, 474 (M+, bromine isotopes).

EXAMPLE 8

(7α,17β) 7-(4-Bromophenyl)thio-estra-1,3,5(10)-
triene-3,17-diol

Prepared by General Procedure 3

M.p. 165–166° C.; $^1$H NMR (DMSO) 9.05 (s, 1 H), 7.50 (d, 2 H, J=8.6 Hz), 7.30 (d, 2 H, J=8.6 Hz), 7.09 (d, 1 H, J=8.8 Hz), 6.53 (dd, 1 H, J=8.6 Hz, 2.6 Hz), 6.37 (d, 1 H, J=2.6 Hz), 4.54 (d, 1 H, J=4.8 Hz), 3.66–3.62 (m, 1 H), 3.56 3.50 (m, 1 H), 3.17 (dd, 1 H, J=17.3 Hz, 4.8 Hz), 2.76 (d, 1 H, J=17.1 Hz), 2.39–2.28 (m, 2 H), 1.85–1.78 (m, 3 H), 1.55–1.40 (m, 2 H), 1.40–1.25 (m, 3 H), 1.10–1.07 (m, 1 H), 0.68 (s, 3 H); IR (KBr) 3390, 2910, 1610 cm$^{-1}$; MS(EI) m/z 460, 458 (M+, Bromine isotopes).

EXAMPLE 9

(7α,17β) 7-{4-[2-(Methoxycarbonyl)-ethenyl]
phenyl}thio-estra-1,3,5(10)-triene-3,17-diol-17-
acetate Prepared by General Procedure 4

M.p. 122–125° C.; $^1$H NMR (CDCl$_3$) 7.65 (d, 1 H, J=16.0 Hz), 7.43 (d, 2 H, J=8.1 Hz), 7.35 (d, 2 H, J=8.3 Hz), 7.20 (d, 1 H, J=8.0 Hz), 6.68 (dd, 1 H, J=8.6 Hz, 2.6 Hz), 6.50 (d, 1 H, J=2.6 Hz), 6.41 (d, 1 H, J=16.0 Hz), 4.74 (dd, 1 H, J=9.2 Hz, 7.9 Hz), 4.62 (br s, 1 H), 3.81 (s, 3 H), 3.69–3.66 (m, 1 H), 3.25 (dd, 1 H, J=16.9 Hz, 2.4 Hz), 2.99 (d, 1 H, J=17.4 Hz), 2.65–2.56 (m, 1 H), 2.41–2.35 (m, 1 H), 2.28–2.18 (m, 1 H), 2.06 (s, 3 H), 1.96–1.85 (m, 2 H), 1.78–1.69 (m, 2 H), 1.61–1.39 (m, 4 H), 0.85 (s, 3 H); IR (KBr) 3400, 2910, 1720, 1620 cm$^{-1}$; MS(EI) m/z 506 (M+).

EXAMPLE 10

(7α,17β) 7-{4-[(E)-2-(N,N-Dimethylcarbamoyl)-
ethenyl]phenyl}thio-estra-1,3,5(10)-triene-3,17-diol Prepared by General Procedure 4

M.p. 152–155° C.; $^1$H NMR (DMSO) 9.05 (s, 1 H), 7.64 (d, 2 H, J=8.3 Hz), 7.41 (d, 1 H, J=15.4 Hz), 7.33 (d, 2 H, J=8.3 Hz), 7.16 (d, 1 H, J=15.6 Hz), 7.10 (d, 1 H, J=8.3 Hz), 6.54 (dd, 1 H, J=8.3 Hz, 2.2 Hz), 6.37 (d, 1 H, J=2.4 Hz), 4.53 (d, 1 H, J=4.8 Hz), 3.75–3.72 (m, 1 H), 3.56–3.51 (m, 1 H), 3.24–3.19 (m, 1 H), 3.14 (s, 3 H), 2.91 (s, 3 H), 2.79 (d, 1 H, J=16.7 Hz), 2.41–2.29 (m, 2 H), 1.86–1.78 (m, 2 H), 1.55–1.42 (m, 2 H), 1.40–1.27 (m, 4 H), 1.22–1.14 (m, 1 H), 0.68 (s, 3 H); IR (KBr) 3420, 2910, 1650 cm$^{-1}$; MS(EI) m/z 478 (M+).

EXAMPLE 11

(7α,17β) 7-{4-[2-(Carboxy)-ethenyl]phenyl}thio-
estra-1,3,5(10)-triene-3,17-diol Prepared by General Procedure 4

M.p. 215–220° C.; $^1$H NMR (DMSO) 13–10 (br s, 1 H), 9.10 (br s, 1 H), 7.59 (d, 2 H, J=8.6 Hz), 7.49 (d, 1 H, J=15.8 Hz), 7.33 (d, 2 H, J=8.4 Hz), 7.09 (d, 1 H, J=8.6 Hz), 6.54 (dd, 1 H, J=8.6 Hz, 2.6 Hz), 6.48 (d, 1 H, J=16.0 Hz), 6.37 (d, 1 H, J=2.4 Hz), 4.54 (br s, 1 H), 3.76 (br s, 1 H), 3.52 (t, 1 H, J=7.7 Hz), 3.28–3.20 (m, 2 H), 2.79 (d, 1 H, J=18.2 Hz), 2.40–2.34 (m, 2 H), 1.88–1.78 (m, 3 H), 1.55–1.50 (m, 2 H), 1.40–1.24 (m, 2 H), 1.22–1.16 (m, 1 H), 0.68 (s, 3 H); IR (KBr) 3300 br, 2900, 1685 cm$^{-1}$; MS(EI) m/z 450 (M+).

EXAMPLE 12

(7α,17β) 7-(4-(4'-Formylbiphenyl)]thio-estra-1,3,5
(10)-triene-3,17-diol

Prepared by General Procedure 6

M.p. 140–145° C.; $^1$H NMR (DMSO) 10.04 (s, 1 H), 9.05 (s, 1 H), 7.98 (d, 2 H, J=8.3 Hz), 7.90 (d, 2 H, J=8.3 Hz), 7.73 (d, 2 H, J=8.3 Hz), 7.46 (d, 2 H, J=8.3 Hz), 7.11 (d, 1 H, J=8.6 Hz), 6.55 (dd, 1 H, J=8.3 Hz, 2.4 Hz), 6.38 (d, 1 H, J=2.4 Hz), 4.54 (d, 1 H, J=4.6 Hz), 3.76–3.73 (m, 1 H), 3.60–3.53 (m, 1 H), 3.23 (dd, 1 H, J=17.6 Hz, 4.2 Hz), 2.83 (d, 1 H, J=16.9 Hz), 2.41–2.32 (m, 2 H), 190–1.80 (m, 3 H), 1.58–1.53 (m, 2 H), 1.41–1.26 (m, 3 H), 1.22–1.18 (m, 1 H), 0.69 (s, 3 H); IR (KBr) 3400 br, 2900, 1700, 1670, 1600 cm$^{-1}$; MS(EI) m/z 484 (M+).

EXAMPLE 13

(7α,17β) 7-{4-[4'-(2-Carboxy)-ethenyl]
biphenyl}thio-estra-1,3,5(10)-triene-3,17-diol
sodium salt Prepared by General Procedure 6

M.p. 219–221° C.; $^1$H NMR 9.05 (br s, 1 H), 7.68 (s, 4 H), 7.65 (d, 2 H, J=8.6 Hz), 7.42 (d, 2 H, J=8.6 Hz), 7.44 (d, 1 H, J=16.3 Hz), 7.42 (d, 2 H, J=8.6 Hz), 7.10 (d, 1 H, J=8.6 Hz), 6.54 (dd, 1 H, J=8.8 Hz, 2.0 Hz), 6.52 (d, 1 H, J=15.8 Hz), 6.39 (d, 1 H, J=2.4 Hz), 4.54 (br s, 1 H), 3.70 (br s, 1 H), 3.58–3.54 (m, 1 H), 3.26–3.22 (m, 1 H), 2.81 (d, H, J=17.4 Hz), 2.42–2.31 (m, 2 H), 1.85–1.78 (m, 3 H), 1.58–1.4 5 (m, 2 H), 1.41–1.30 (m, 3 H), 1.21–1.18 (m, 1 H), 0.69 (s, 3 H); IR (KBr) 3400, 2900, 1700, 1630 cm$^{-1}$; MS FAB m/z 525 (M-H-).

EXAMPLE 14

(7α,17β) 3-Methoxy-7-{4-[2-(piperdin-1-yl)]
ethoxyphenyl}thio-estra-1,3,5(10)-triene-17-ol-17-
acetate Prepared by General Procedure 5

M.p. 60–62° C.; $^1$H NMR (CDCl$_3$) 7.35 (d, 2 H, J=8.8 Hz), 7.24 (d, 1 H, J=8.2 Hz), 6.84 (d, 2 H, J=8.8 Hz), 6.76 (dd, 1 H, J=8.8 Hz, 2.9 Hz), 6.58 (d, 1 H, J=2.6 Hz), 4.75 (dd, 1 H, J=9.0 Hz, 7.9 Hz), 4.09 (t, 2 H, J=6.2 Hz), 3.78 (s, 3 H), 3.41–3.37 (m, 1 H), 3.12 (dd, 1 H, J=16.9 Hz, 4.6 Hz), 2.96 (d, 1 H, J=16.9 Hz), 2.77 (t, 2 H, J=6.2 Hz), 2. 69–2.60 (m, 1 H), 2.55–2.46 (m, 3 H), 2.41–2.36 (m, 1 H), 2.31–2.20 (m, 1 H), 2.06 (s, 3 H), 1.90–1.75 (m, 4 H), 1.67–1.52 (m, 5 H), 1.50–1.38 (m, 4 H), 1.25 (s, 2 H), 0.83 (s, 3 H); IR (KBr) 3450, 2920, 1735 cm$^{-1}$; MS FAB m/z 564 (M+H$^+$).

EXAMPLE 15

(7α,17β) 3-Methoxy-7-{4-[2-(piperdin-1-yl)] ethoxyphenyl}thio-estra-1,3,5(10)-triene-17-ol Prepared by General Procedure 5

M.p. 116–118° C.; $^1$H NMR (DMSO) 7.29 (d, 2 H, J=8.8 Hz), 6.91 (d, 1 H, J=8.8 Hz), 6.91 (d, 2 H, J=8.8 Hz), 6.71 (dd, 1 H, J=9.0 Hz, 2.9 Hz), 6.56 (d, 1 H, J=2.9 Hz), 4.54 (d, 1 H, J=4.8 Hz), 4.04 (t, 2 H, J=5.5 Hz), 3.68 (s, 3 H), 3.58–3.53 (m, 1 H), 3.42–3.37 (m, 1 H), 3.16–3.07 (m, 1 H), 2.83 (d, 1 H, J=17.0 Hz), 2.65–2.61 (m, 2 H), 2.47–2.30 (m, 4 H), 1.94–1.86 (m, 3 H), 1.61–1.44 (m, 7 H), 1.41–1.24 (m, 6 H), 1.22–1.16 (m, 2 H), 0.67 (s, 3 H); IR (KBr) 3400, 2910, 1620, 1600 cm$^{-1}$; MS(EI) m/z 521 (M$^+$).

EXAMPLE 16

(7α,17β) 7-[10-(N-Butyl-N-methyl-carbamoyl)-decyl]thio-3,17-dihydroxy-estra-1,3,5(10)-triene-6-one Prepared by General Procedure 2

M.p. N/A (foam); $^1$H NMR (CDCl$_3$) (amide rotamers in spectrum) 7.95, 7.91 (2 s, 1 H), 7.63 (t, 1 H, J=3.1 Hz), 7.26, 7.24 (2 s, 1 H), 7.07, 7.05 (2 d, 1 H, J=2.9 Hz, J=2.6 Hz), 3.82–3.77 (m, 1 H), 3.41–3.37 (m, 2 H), 3.30–3.26 (m, 1 H), 3.00, 2.95 (2 s, 3 H), 2.78, 2.76 (2 t, 1 H, J=11.2 Hz), 2.65–2.50 (m, 2 H), 2.43–2.14 (m, 5 H), 1.97, 1.93 (2 t, 1 H, J=3.3 Hz), 1.80–1.42 (m, 10 H), 1.40–1.16 (m, 17 H), 0.96, 0.92 (2 t, 3 H, J=7.2 Hz), 0.79 (s, 3 H); IR (KBr) 3400 br, 2910, 1680, 1620 cm$^{-1}$; MS(CI) m/z 572 (M+H$^+$). (M+H+).

EXAMPLE 17

(6α,7α,17β) 7-[10-(N-Butyl-N-methyl-carbamoyl)-decyl]thio-estra-1,3,5(10)-triene-3,6,17-triol Prepared by General Procedure 2

M.p. N/A (Foam); $^1$H NMR (CDCl$_3$) (amide rotamers in spectrum) 7.26–7.21 (m, 1 H), 7.09 (d, 1 H, J=8.8 Hz), 6.77, 6.71 (2s, 1 H), 6.72 (dd, 1 H, J=8.6 Hz, 2.6 Hz), 4.83 (dd, 1 H, J=12.3 Hz, 4.8 Hz), 3.81 (m, 1 H), 3.37, 3.27 (2t, 1 H, J=4.6 Hz, 7.2 Hz), 3.17, 3.15 (2 d, 1 H, J=2.0 Hz, 1.8 Hz), 2.98, 2.93 (2 br s, 3 H), 2.65 (t, 3 H, J=6.8 Hz), 2.59 (dt, 1 H, J=10.8 Hz, 3.7 Hz), 2.48–2.36 (m, 3 H), 2.21–2.12 (m, 1 H), 1.94–1.83 (m, 2 H), 1.78–1.38 (m, 14 H), 1.38–1.24 (m, 14 H), 0.99–0.86 (m, 3 H), 0.81 (s, 3 H); IR (KBr) 3400 br, 2920, 1620 cm$^{-1}$; MS(EI) m/z 573 (M$^+$).

EXAMPLE 18

(7α,17β) 7-[10-(N-Butyl-N-methyl-carbamoyl)-decyl]thio-estra-1,3,5(10)-triene-3,17-diol Prepared by General Procedure 7

M.p. 71–75° C.; $^1$H NMR (CDCl$_3$) 7.14 (d, 1 H, J=7.9 Hz), 6.68 (dd, 1 H, J=8.3 Hz, 2.6 Hz), 6.62 (d, 1 H, J=2.4 Hz), 3.78 (t, 1 H, J=8.3 Hz), 3.42–3.33 (m, 1 H), 3.32–3.18 (m, 1 H), 3.12–3.07 (m, 1 H), 3.04–2.90 (m, 4 H), 2.56–2.47 (m, 3 H), 2.38–2.29 (m, 3 H), 2.21–2.10 (m, 1 H), 1.94–1.85 (m, 1 H), 1.75 (dt, 1 H, J=11.2 Hz, 2.4 Hz), 1.71–1.45 (m, 10 H), 1.40–1.12 (m, 19 H), 1.01–0.88 (m, 3 H), 0.78 (s, 3 H); IR (KBr) 3350, 2910, 1620 cm$^{-1}$; MS(CI) m/z 558 (M+H$^+$).

What is claimed is:

1. A compound of formula I having the stucture

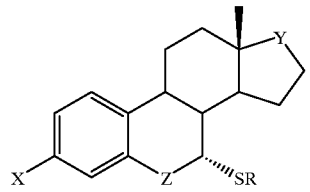

I wherein:

R is

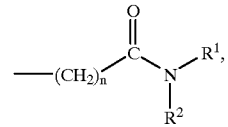

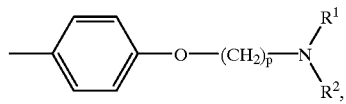

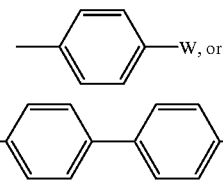

$R^1$ and $R^2$ are each, independently, alkyl of 1–6 carbon atoms, or are alkyl groups which are taken together to form a 5–7 membered saturated heterocycle;

X is hydroxy, alkoxy of 1–6 carbon atoms, or —OC(O)$R^3$;

W is

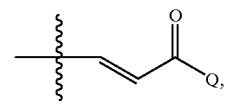

hydroxy, alkyl of 1–6 carbon atoms, halogen, —CF$_3$, alkoxy of 1–6 carbon atoms, —CHO, cyano, alkylcarbonyl of 2–7 carbon atoms, alkoxycarbonyl of 2–7 carbon atoms, amino, alkylamino of 1–6 carbon atoms, dialkylamino of 1–6 carbon atoms per alkyl group, trifluoromethoxy, hydroxyalkyl of 1–6 carbon atoms, alkoxyalkyl of 2–12 carbon atoms, —CN, —SO$_3$H, or —CO$_2$H;

$R^3$ is alkyl of 1–6 carbon atoms;

Z is

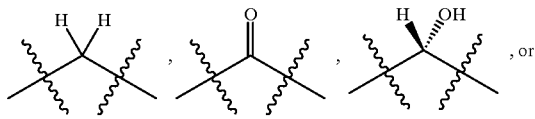

-continued

Y is

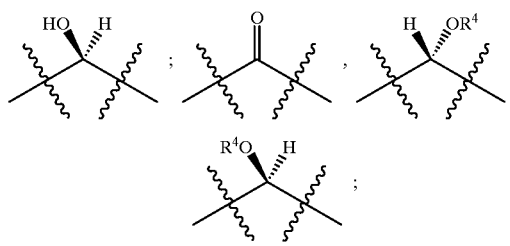

R[4] is hydrogen, alkyl of 1–6 carbon atoms, alkoyl of 2–7 carbon atoms, or benzoyl;

Q is hydrogen, —OR[5], or —NR[6]R[7];

R[5] is hydrogen or alkyl of 1–6 carbon atoms;

R[6] and R[7] are each, independently, alkyl of 1–6 carbon atoms, or are alkyl groups which are taken together to form a 5–7 membered saturated heterocycle;

n=4–12; and p=2–6;

or a pharmaceutically acceptable salt thereof.

2. The compound according to claim 1, wherein Z is

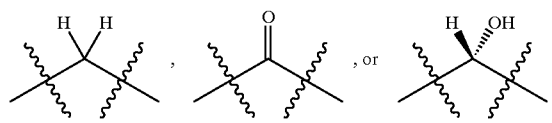

or a pharmaceutically acceptable salt thereof.

3. The compound according to claim 1, wherein Z is

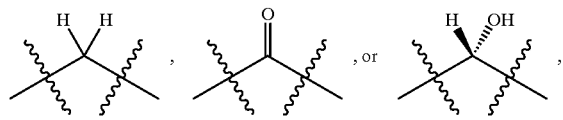

and Y is

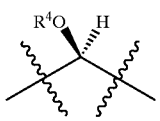

or a pharmaceutically acceptable salt thereof.

4. The compound according to claim 3, wherein R[4] is hydrogen or alkoyl of 2–7 carbon atoms or a pharmaceutically acceptable salt thereof.

5. The compound according to claim 1, wherein R is

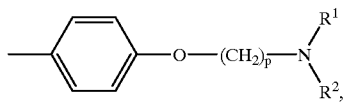

-continued

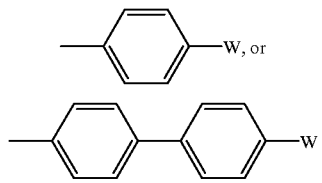

or a pharmaceutically acceptable salt thereof.

6. The compound according to claim 1, wherein R is

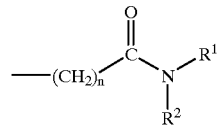

or a pharmaceutically acceptable salt thereof.

7. The compound according to claim 1, which is (7α,17β) 17-acetoxy-3-hydroxy-7-(4-hydroxyphenyl)thio-estra-1,3,5(10)-triene-6-one or a pharmaceutically acceptable salt thereof.

8. The compound according to claim 1, which is (7α,17β) 3,17-dihydroxy-7-(4-hydroxyphenyl)thio-estra-1,3,5(10)-triene-6-one or a pharmaceutically acceptable salt thereof.

9. The compound according to claim 1, which is (6α,7α,17β) 7-(4-hydroxyphenyl)thio-estra-1,3,5(10)-triene-3,6,17-triol or a pharmaceutically acceptable salt thereof.

10. The compound according to claim 1, which is (7α,17β) 7-(4-hydroxyphenyl)thio-estra-1,3,5(10)-triene-3,17-diol or a pharmaceutically acceptable salt thereof.

11. The compound according to claim 1, which is (7α,17β) 17-acetoxy-7-(4-bromophenyl)thio-3-hydroxy-estra-1,3,5(10)-trien-6-one or a pharmaceutically acceptable salt thereof.

12. The compound according to claim 1, which is (7α,17β) 7-(4-bromophenyl)thio-3,17-dihydroxy-estra-1,3,5(10)-trien-6-one or a pharmaceutically acceptable salt thereof.

13. The compound according to claim 1, which is (6α,7α,17β) 7-(4-bromophenyl)thio-estra-1,3,5(10)-triene-3,6,17-triol or a pharmaceutically acceptable salt thereof.

14. The compound according to claim 1, which is (7α,17β) 7-(4-bromophenyl)thio-estra-1,3,5(10)-triene-3,17-diol or a pharmaceutically acceptable salt thereof.

15. The compound according to claim 1, which is (7α,17β) 7-{4-[2-(methoxycarbonyl)-ethenyl]phenyl}thio-estra-1,3,5(10)-triene-3,17-diol-17-acetate or a pharmaceutically acceptable salt thereof.

16. The compound according to claim 1, which is (7α,17β) 7-{4-[(E)-2-(N,N-dimethylcarbamoyl)-ethenyl]phenyl}thio-estra-1,3,5(10)-triene-3,17-diol or a pharmaceutically acceptable salt thereof.

17. The compound according to claim 1, which is (7α,17β) 7-{4-[2-(carboxy)-ethenyl]phenyl}thio-estra-1,3,5(10)-triene-3,17-diol or a pharmaceutically acceptable salt thereof.

18. The compound according to claim 1, which is (7α,17β) 7-[4-(4'-formylbiphenyl)]thio-estra-1,3,5(10)-triene-3,17-diol or a pharmaceutically acceptable salt thereof.

19. The compound according to claim 1, which is (7α,17β) 7-{4-[4'-(2-carboxy)-ethenyl]biphenyl}thio-estra-1,3,5(10)-triene-3,17-diol or a pharmaceutically acceptable salt thereof.

20. The compound according to claim 1, which is (7α,17β) 7-{4-[4'-(2-carboxy)-ethenyl]biphenyl}thio-estra-1,3,5(10)-triene-3,17-diol sodium salt.

21. The compound according to claim 1, which is (7α, 17β) 3-methoxy-7-{4-[2-(piperidin-1-yl)]ethoxyphenyl}thio-estra-1,3,5(10)-triene-17-ol-17-acetate or a pharmaceutically acceptable salt thereof.

22. The compound according to claim 1, which is (7α, 17β) 3-methoxy-7-{4-[2-(piperidin-1-yl)]ethoxyphenyl}thio-estra-1,3,5(10)-triene-17-ol or a pharmaceutically acceptable salt thereof.

23. The compound according to claim 1, which is (7α, 17β) 7-[10-(N-butyl-N-methyl-carbamoyl)-decyl]thio-3,17-dihydroxy-estra-1,3,5(10)-triene-6-one or a pharmaceutically acceptable salt thereof.

24. The compound according to claim 1, which is (6α, 7α,17β) 7-[10-(N-butyl-N-methyl-carbamoyl)-decyl]thio-estra-1,3,5(10)-triene-3,6,17-triol or a pharmaceutically acceptable salt thereof.

25. The compound according to claim 1, which is (7α, 17β) 7-[10-(N-butyl-N-methyl-carbamoyl)-decyl]thio-estra-1,3,5(10)-triene-3,17-diol or a pharmaceutically acceptable salt thereof.

26. A pharmaceutical composition which comprises a compound of formula I having the structure

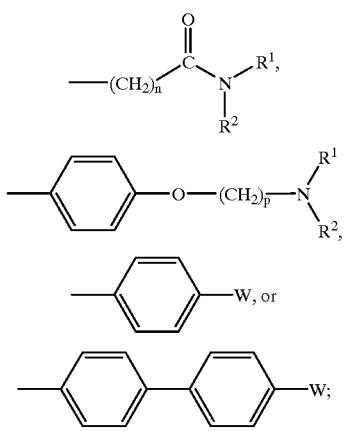

I wherein:

R is

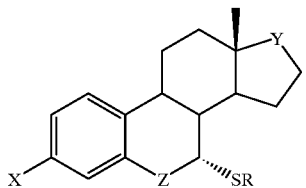

$R^1$ and $R^2$ are each, independently, alkyl of 1–6 carbon atoms, or are alkyl groups which are taken together to form a 5–7 membered saturated heterocycle;

X is hydroxy, alkoxy of 1–6 carbon atoms, or —OC(O)$R^3$;

W is

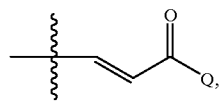

hydroxy, alkyl of 1–6 carbon atoms, halogen, —CF$_3$, alkoxy of 1–6 carbon atoms, —CHO, cyano, alkylcarbonyl of 2–7 carbon atoms, alkoxycarbonyl of 2–7 carbon atoms, amino, alkylamino of 1–6 carbon atoms, dialkylamino of 1–6 carbon atoms per alkyl group, trifluoromethoxy, hydroxyalkyl of 1–6 carbon atoms, alkoxyalkyl of 2–12 carbon atoms, —CN, —SO$_3$H, or —CO$_2$H;

$R^3$ is alkyl of 1–6 carbon atoms;

Z is

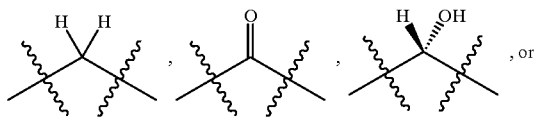

Y is

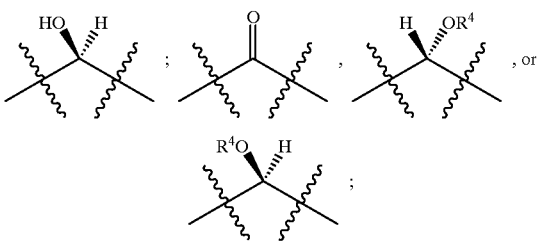

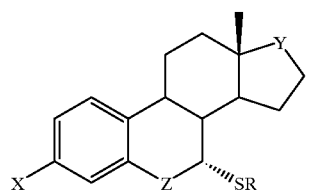

$R^4$ is hydrogen, alkyl of 1–6 carbon atoms, alkoyl of 2–7 carbon atoms, or benzoyl;

Q is hydrogen, —OR$^5$, or —NR$^6$R$^7$;

$R^5$ is hydrogen or alkyl of 1–6 carbon atoms;

$R^6$ and $R^7$ are each, independently, alkyl of 1–6 carbon atoms, or are alkyl groups which are taken together to form a 5–7 membered saturated heterocycle;

n=4–12; and p=2–6;

or a pharmaceutically acceptable salt thereof, and a pharmaceutical carrier.

27. A method of providing estrogen replacement therapy or treating estrogen deficiency in a mammal in need thereof, which comprises administering an estrogenic amount of a compound of formula I having the structure

I wherein:

R is

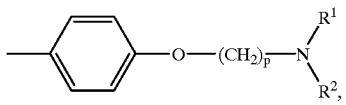

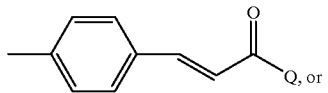

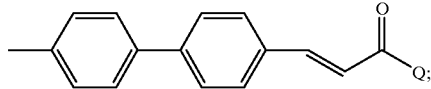

R¹ and R² are each, independently, alkyl of 1–6 carbon atoms, or are alkyl groups which are taken together to form a 5–7 membered saturated heterocycle;

X is hydroxy, alkoxy of 1–6 carbon atoms, or —OC(O)R³;

R³ is alkyl of 1–6 carbon atoms;

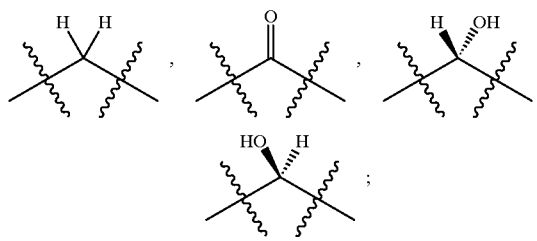

Y is

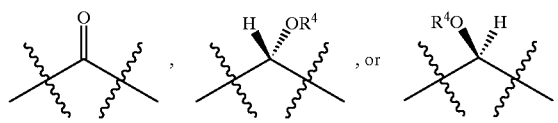

R⁴ is hydrogen, alkyl of 1–6 carbon atoms, alkoyl of 2–7 carbon atoms, or benzoyl;

Q is hydrogen, —OR⁵, or —NR⁶R⁷;

R⁵ is hydrogen or alkyl of 1–6 carbon atoms;

R⁶ and R⁷ are each, independently, alkyl of 1–6 carbon atoms, or are alkyl groups which are taken together to form a 5–7 membered saturated heterocycle; and p=2–6;

or a pharmaceutically acceptable salt thereof.

28. A method of treating or inhibiting osteoporosis in a mammal in need thereof which comprises administering an anti-osteoporosis effective amount of a compound of formula I having the structure

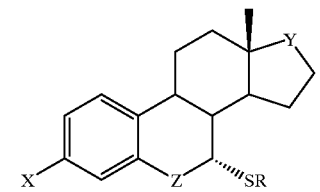

wherein:

R is

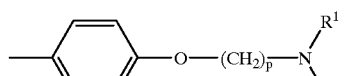

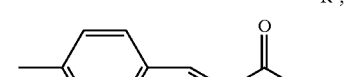

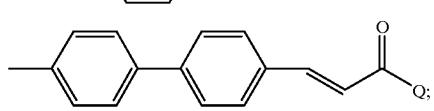

R¹ and R² are each, independently, alkyl of 1–6 carbon atoms, or are alkyl groups which are taken together to form a 5–7 membered saturated heterocycle;

X is hydroxy, alkoxy of 1–6 carbon atoms, or —OC(O)R³;

R³ is alkyl of 1–6 carbon atoms;

Z is

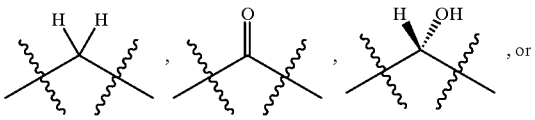

Y is

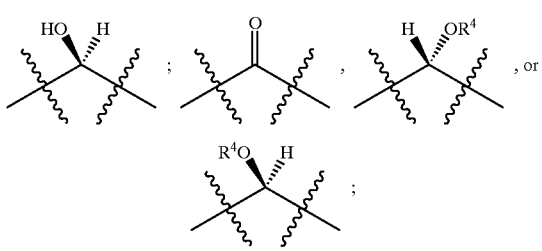

R⁴ is hydrogen, alkyl of 1–6 carbon atoms, alkoyl of 2–7 carbon atoms, or benzoyl;

Q is hydrogen, —OR⁵, or —NR⁶R⁷;

R⁵ is hydrogen or alkyl of 1–6 carbon atoms;

R⁶ and R⁷ are each, independently, alkyl of 1–6 carbon atoms, or are alkyl groups which are taken together to form a 5–7 membered saturated heterocycle; and p=2–6;

or a pharmaceutically acceptable salt thereof.

29. A method of treating or inhibiting atherosclerosis in a mammal in need thereof which comprises administering an anti-atherosclerosis effective amount of a compound of formula I having the stucture

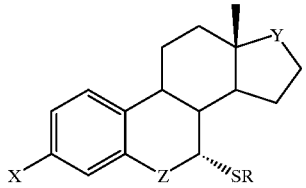

wherein:

R is

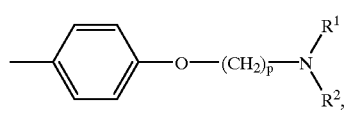

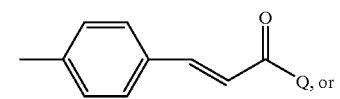

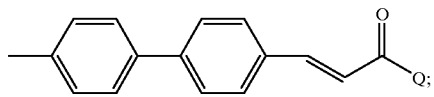

$R^1$ and $R^2$ are each, independently, alkyl of 1–6 carbon atoms, or are alkyl groups which are taken together to form a 5–7 membered saturated heterocycle;

X is hydroxy, alkoxy of 1–6 carbon atoms, or —OC(O)$R^3$;

$R^3$ is alkyl of 1–6 carbon atoms;

Z is

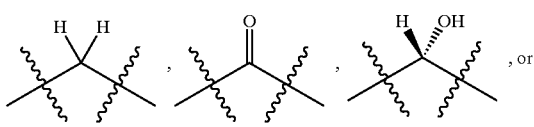

Y is

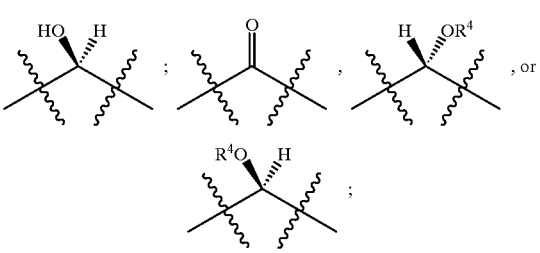

$R^4$ is hydrogen, alkyl of 1–6 carbon atoms, alkoyl of 2–7 carbon atoms, or benzoyl;

Q is hydrogen, —OR$^5$, or —NR$^6$R$^7$;

$R^5$ is hydrogen or alkyl of 1–6 carbon atoms;

$R^6$ and $R^7$ are each, independently, alkyl of 1–6 carbon atoms, or are alkyl groups which are taken together to form a 5–7 membered saturated heterocycle; and p=2–6;

or a pharmaceutically acceptable salt thereof.

30. A method of providing antiestrogen therapy in a mammal in need thereof which comprises administering to said mammal an antiestrogen amount of a compound of formula I having the structure

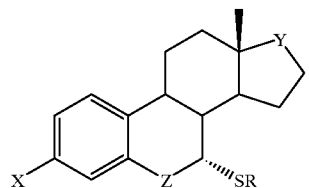

wherein:

R is

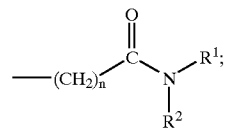

$R^1$ and $R^2$ are each, independently, alkyl of 1–6 carbon atoms, or are alkyl groups which are taken together to form a 5–7 membered saturated heterocycle;

X is hydroxy, alkoxy of 1–6 carbon atoms, or —OC(O)$R^3$;

$R^3$ is alkyl of 1–6 carbon atoms;

Z is

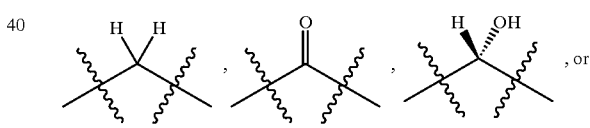

Y is

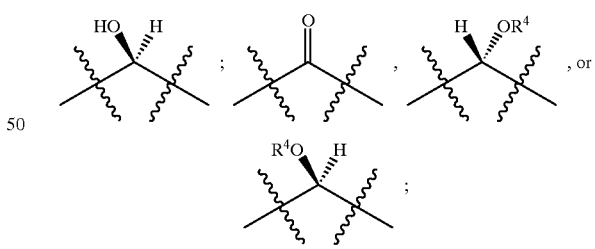

$R^4$ is hydrogen, alkyl of 1–6 carbon atoms, alkoyl of 2–7 carbon atoms, or benzoyl; and n=4–12;

or a pharmaceutically acceptable salt thereof.

* * * * *